United States Patent [19]

Ozdoba et al.

[11] Patent Number: 5,290,962
[45] Date of Patent: Mar. 1, 1994

[54] METHOD FOR PREPARATION OF ANTI-CALKING COATING WITH PIGMENT THEREIN

[75] Inventors: Dale M. Ozdoba, Edmonton, Canada; Reynaldo G. Araga, Long Beach, Calif.

[73] Assignee: Exxon Chemical Patents Inc., Linden, N.J.

[21] Appl. No.: 403,539

[22] Filed: Sep. 6, 1989

[51] Int. Cl.$^5$ .............................. C07C 51/00
[52] U.S. Cl. .................... 554/156; 564/157; 564/158; 252/302; 252/367; 427/212
[58] Field of Search ............... 423/635, 636; 427/212; 252/302, 367; 554/156, 157, 158

[56] References Cited

U.S. PATENT DOCUMENTS

| | | | |
|---|---|---|---|
| 3,966,853 | 9/1974 | Osako et al. | 264/13 |
| 4,036,979 | 4/1976 | Asato | 424/275 |
| 4,605,550 | 6/1984 | Trill | 424/22 |
| 4,736,683 | 8/1986 | Bachman et al. | 102/290 |

*Primary Examiner*—Paul J. Thibodeau
*Assistant Examiner*—R. Follett
*Attorney, Agent, or Firm*—E. F. Sherer

[57] ABSTRACT

A coating composition useful on a variety of substrates, and particularly as a coating for ammonium nitrate which exhibit a reduced tendency to cake or dust once applied to the surface of a substrate. In one embodiment, the composition is composed of magnesium stearate and an effective amount of magnesium oxide, i.e. 10-15% by total weight of the coating composition, to substantially minimize or reduce the tendency of the composition to cake or dust, particularly after the coating composition is applied to the substrate. The composition preferably is colored by incorporating pigment in a reactant mixture of stearic acid and magnesium oxide before completion of the reaction. As a result the pigment is entrapped in a matrix formed by the magnesium stearate and magnesium oxide so that discoloration by contact with the coating composition, for example on the coated substrate, does not readily occur. The reaction is conducted in two stages: in the first stage magnesium oxide, a relatively small amount of stearic acid, a reaction catalyst and water are mixed at about 750° C. to uniformly disperse the magnesium oxide in the resultant slurry; then, in the second stage, the temperature is raised to 80°-85° C. and the balance of the stearic acid is added and reacted to form the desired reaction product composition of the present invention. The pigment is added to the reaction mixture, preferably in the form of an aqueous surfactant solution, before completion of the reaction so as to become entrapped in a matrix formed by the magnesium stearate and magnesium oxide components of the reaction product composition.

19 Claims, No Drawings

METHOD FOR PREPARATION OF ANTI-CALKING COATING WITH PIGMENT THEREIN

BACKGROUND OF THE INVENTION

1. Field of the Invention

The present invention relates to compositions useful as coatings, particularly powder coatings which do not tend to cake or dust after being applied to the surface of a substrate, and coating compositions containing pigments which do not tend to discolor objects with which it comes into contact. The present invention is also directed to composite products of a substrate having a surface at least partially coated with such coatings, and to processes for the preparation of such coating compositions.

2. Discussion of Background and Material Information

The agricultural chemical industry encompasses a wide range of products originally developed for agricultural application, but currently expanded to diverse uses. For example, synthesized fertilizers were and remain an important agricultural product, being basic or essential chemical compounds for use by farmers in growing crops. Synthesized fertilizers often are composed of nitrogen, phosphorous and potassium-containing compounds. Although the primary purpose may be to deliver specific chemicals into the plant growing environment, it has been recognized that other chemicals, in smaller amounts (therefore termed "trace elements"), serve a useful purpose. Therefore, the synthetic fertilizer compositions will often contain these elements in addition to the primary chemicals identified above.

A synthesized fertilizer may be applied to the soil as well as directly to the plant itself. In the manufacture of such fertilizers, the relative ratios of these and other chemicals are controlled for particular applications. When fertilizers are applied to growing crops, either liquid or solid media forms can be used. Solid forms suitable for this purpose are typically either prills or granules. Although in either case, each form is approximately spherical granules are formed by an agglomerating process building layer upon layer whereas prills are formed by the solidification of a single droplet.

As the technology for producing such solid fertilizers has progressed, agricultural chemical manufacturers discovered that the coatings for prill or granule materials can be formulated from substances in which additional materials or additives, which may be referred to herein as "agricultural chemical additives", such as trace elements necessary for growing crops, biocides, herbicides, fungicides, nematicides, acaricides, bird repellants, growth regulators, soil structure improvement agents, pesticides, helpful biological species such as bacteria, or other such materials, are incorporated.

More recently, the chemical compounds normally used as fertilizers have been formulated to contain combinations of chemicals useful in chemical reactions other than those reactions which contribute to the growth of a plant. Thus, agricultural chemicals and derivatives from agricultural chemicals have been discovered to be particularly suitable for use beyond traditional farming applications, such as the use of ammonium nitrate as an explosive.

Such chemicals, however, often require special handling because of their reactive nature. Therefore, procedures involving the treatment and handling of chemicals and materials in manufacturing processes used to produce such combinations of chemicals was and remains an important area of technology, particularly for reasons of safety. The coating technology useful in the manufacture, handling, storage and application of agricultural chemicals has, therefore, become important for other industrial chemicals as well.

In the agricultural fertilizer industry, coatings on fertilizer solids have been used as anti-caking agents to prevent individual solids particles from caking together during the manufacturing, storing, handling and use. Such caking may result due at least in part to physical or chemical processes causing the individual particles to bond or stick to each other. Caking also tends to occur when moisture comes into contact with the particles.

Historically, clay has been the most commonly used anti-caking powder for coating fertilizer solids such as ammonium nitrate granules. Such clay coating may be applied by mixing fertilizer granules with clay particles so that the clay particles stick to the exterior surface of the fertilizer granule. However, the use of clay gives rise to undesirable clay dust suspension in the surrounding environment when the granules are handled, used or otherwise moved since such movement can cause dust to separate from the fertilizer granule. Also, if suitable clay is not close at hand to the manufacturing site, the cost of clay can become a factor due to the affect of its weight on shipping costs.

In recent years, commercial grade magnesium stearate powder has been employed as an alternative to clay for coating ammonium nitrate fertilizer granules. The designation of "commercial grade" indicates that the powder may have some impurities in the powder, at least more than might be found in a "pharmaceutical grade". The magnesium stearate coating has been used for this purpose in view of its anti-caking properties and reduced dust generation which are generally considered to be an improvement over clay.

The commercial grade magnesium stearate powder suitable for this purpose is normally made by a conventional "precipitation" or "fusion" processes. In precipitation, the materials to be reacted are dissolved in liquid and are brought together to react to form an undissolved solid which is recovered from the liquid. In fusion, melted materials are mixed together to react and the reaction product is then cooled to a solid. In either case, these processes involve reacting stearic acid with magnesium oxide. The commercial grade magnesium stearate powder produced by such reactions normally contains about 6–8% weight unreacted excess magnesium oxide (theoretically 6.8% MgO).

Although magnesium stearate powder is considered to be an improvement over clay as a fertilizer coating, commercial grade magnesium stearate powder has two undesirable characteristics which are pertinent to the present invention. Firstly, magnesium stearate powder is relatively expensive and thus contributes substantially to the cost of the fertilizer. Secondly, magnesium stearate powder is white in color. Consequently a composite fertilizer product, for example white ammonium nitrate granules coated with white commercial grade magnesium stearate, is indistinguishable from other white fertilizer, such as urea. This lack of distinguishing color is undesirable and potentially hazardous because it can lead to inadvertent mixing of, for example, the ammonium nitrate granules with a second fertilizer which can result in adhesion or "mudding" of the mix which would become extremely hydroscopic in nature and result in mushing because of the retained moisture.

In a prior attempt to color commercial grade magnesium stearate powder coating material, the assignee of the present invention physically mixed dry green pigment powder with magnesium stearate powder. However, there were three significant problems associated with that effort. Firstly, the distribution of the coloring agent pigment was variable, and it was difficult if not practically impossible to effect an homogenous distribution of pigment to result in a uniform color. Secondly, a relatively large concentration of pigment was required, which affected the cost of the end product. Thirdly, and most significantly, when the coating material was applied to a substrate the pigment had a tendency to rub off easily and, thus, discolored anything with which it came into contact.

U.S. Pat. No. 3,966,853 and U.S. Pat. No. 4,736,683, relate to the use of magnesium oxide to improve the physical prill properties, such as hardness and resistance to caking of ammonium nitrate prills, such as ANFO explosives. In those patents, magnesium stearate, calcium stearate and other metallic carboxylic acid salts are mixed with particulate ammonium nitrate in drums to improve physical properties.

U.S. Pat. No. 4,036,979 is directed to wherein the use of magnesium stearate and zinc stearate as a lubricant wherein a method is disclosed for improving feed efficiency and accelerating animal growth, the lubricating property being used on an implant.

U.S. Pat. No. 4,605,550 relates to controlled or delayed release formulations in which magnesium stearate is used as a lubricant for the die wall.

In the field of agricultural and industrial chemicals, however, there exists a need to provide a coating for substrates, such as chemical particles, which is relatively inexpensive, is improved with respect to reducing dust generation, experiences minimal caking, and which can be tinted using a color other than white or the base color of the substrate being coated, for example so that the coating will distinguish the coated chemical particle from other granular fertilizers or chemicals.

Notwithstanding attempts to provide an improved coating for agricultural and industrial chemicals, and specifically for improved magnesium stearate coatings, prior to the present invention, there was still a need for a magnesium stearate coating wherein the coating material would not cake or dust and particularly such a magnesium stearate coating which included a pigment which had a reduced tendency to transfer color to an object which comes into contact with the pigmented coating composition or a substrate coated with such a pigmented coating composition.

The present invention is believed to overcome the problems and disadvantages discussed above by providing an economical and efficient coating composition for substrates which prevents caking and minimizes dusting and permits coloration of the coating composition without subsequent discoloration of objects which come into contact with the coating composition.

SUMMARY OF THE INVENTION

The present invention is directed to a composition which has been discovered to be particularly useful for coating various substrates because of its properties which prevent caking and dusting of the composition after it has been applied to a surface of the substrate.

The composition of the present invention is composed of magnesium stearate and magnesium oxide present in an amount within the range of about 10-15% by total weight of the coating composition which is effective for this purpose.

The coating composition of the present invention is prepared by reacting a slurry of reactants, including stearic acid and an excess amount of magnesium oxide to permit a substantially complete reaction of stearic acid with magnesium oxide, to produce a reaction product composition including magnesium stearate and about 10-15% by total weight of magnesium oxide.

The present invention is also directed to a pigmented composition composed of magnesium stearate and magnesium oxide, and a pigment entrapped by the magnesium stearate and magnesium oxide so as to substantially minimize or prevent color of the pigment from transferring to an object with which the composition comes into contact which is advantageous in minimizing or substantially preventing unintentional or undesired discoloration of such object.

The composition of magnesium stearate and magnesium oxide entrapping a pigment in accordance with the present invention is preferably in the form of a powder including particles wherein the magnesium stearate and magnesium oxide form a matrix in which the pigment is entrapped.

The composition of magnesium stearate and magnesium oxide entrapping a pigment in accordance with the present invention is produced by a process wherein the pigment is introduced to the reactants, preferably in a slurry, prior to completion of the reaction of stearic acid with magnesium oxide to produce a reaction product composition of magnesium stearate, magnesium oxide and the entrapped pigment.

The compositions produced in accordance with the present invention have been discovered to be suitable for use in coating a variety of substrates including agricultural and industrial chemicals, such as ammonium nitrate prills, as well as plastic articles, such as extruded pipes.

DETAILED DESCRIPTION OF THE INVENTION

The present invention has been developed in an attempt to improve the coating of substrates, and particularly particulate substrates, such as chemicals, and specifically ammonium nitrate particles, such as prills or granules, to reduce caking or fusion thereof. Although the detailed description and examples of the present invention may identify ammonium nitrate prills as the substrate, it should be understood that the coating compositions, for example in the forms of powder and particles of the present invention will find application to substrates other than ammonium nitrate prills, particularly those substrates for which conventional magnesium stearate powder has already been found to be useful and, therefore, the scope of the invention is contemplated to be broader than for use with granular ammonium nitrates. For example, the present invention has the versatility to be used as a lubricant in the manufacture of plastic pipes.

In one embodiment, the present invention involves a coating composition composed of magnesium stearate and an amount of magnesium oxide, preferably in the form of a powder wherein the amount of magnesium oxide, i.e., within the range of about 10-15% by total weight of the composition, is effective to minimize or prevent caking and dusting, and the process for making such a composition.

The magnesium stearate powder composition of the present invention is the reaction product formed in a reaction involving excess amount of magnesium oxide and stearic acid. The amount of magnesium oxide reactant used should be sufficient to ensure substantially complete reaction with the stearic acid reactant to form magnesium stearate and still have an amount of magnesium oxide remaining as a filler in the product. This works to an economic advantage since the total cost of the powder will be less than if no magnesium oxide was left. Specifically, the total content of magnesium oxide in the reaction mixture is about 10-15% by total weight of the reaction mixture, thereby providing an excess of magnesium oxide (relative to the magnesium oxide content of commercial grade magnesium stearate) in the reaction product in the range of about 2-9%, and preferably 3.2 to 8.2%, by total weight. The reaction product of magnesium stearate produced in accordance with the present invention, therefore, is considered to include such excess of magnesium oxide and is also referred to as a composition of magnesium stearate and magnesium oxide.

If the total magnesium oxide content in the reaction product powder is greater than about 15% by weight, however, it has been discovered that the anti-caking capability of a coating made with such powder deteriorates. If the magnesium oxide content is less than about 10% by weight, the anti-caking and anti-dusting characteristics of the coating deteriorate.

Another aspect of the present invention is a process for producing a magnesium stearate-magnesium oxide composition which involves:

forming a slurry by agitating a predetermined amount of stearic acid, an excess amount of magnesium oxide (relative to the amount required for complete reaction of the stearic acid), a catalyst, and water at a temperature and for a period of time sufficient to uniformly disperse the magnesium oxide in the resultant slurry;

admixing additional stearic acid to produce magnesium stearate containing a sufficient excess of magnesium oxide following the completion of the reaction so that the resultant reaction product does not tend to cake or dust;

digesting the reactants for a sufficient retention time and at a sufficient temperature to react substantially all the stearic acid and convert the same into magnesium stearate; and recovering a composition of magnesium stearate and excess magnesium oxide as a reaction product in liquid or solid form.

As used herein, "digesting the reactants means to further react the reactants or to permit the reaction to continue while continuing agitation. The "catalyst" used in accordance with the present invention is an agent which acts as a dispersing agent for dispersing the magnesium oxide particles in the mixture to enhance a more complete reaction. A preferred agent which is used as a catalyst for purposes of the present invention is an organic acid, such as weak carboxylic acids, with hydroxy acids such as citric acid being most preferred, although other dispersing agents useful as a process aid may be used.

In a preferred embodiment, the present invention is a process for producing a magnesium stearate/magnesium oxide composition which involves:

forming a slurry by agitating magnesium oxide, a catalyst, a predetermined amount of stearic acid, and water at a temperature within the range of about 70°-80° C., and preferably at about 75° C., for a sufficient time to uniformly disperse magnesium oxide in the resultant slurry;

admixing additional stearic acid to produce a reaction mixture including an excess of about 10-15% magnesium oxide;

digesting the reactants at a higher temperature less than about 85° C. and preferably in the range of about 80° C.-85° C. for a sufficient retention time to react substantially all the stearic acid to produce a reaction product of magnesium stearate and excess magnesium oxide in an amount within the range of about 10-15% by total weight of the reaction product; and recovering the reaction product as a powder.

Standard techniques for mixing, agitating and heating may be used. Recovering the reaction product may involve filtering, drying and then recovering the reaction product as a powder.

Another aspect of the present invention, relates to the discovery that undesired gelling of the reaction mixture occurred when relatively large amounts of magnesium oxide were used and the reaction was carried out in one step at a more conventional temperature of at least about 85° C. In accordance with the present invention, it was discovered that gelling could be avoided by carrying out the reaction in two stages, as previously described.

In another embodiment of the present invention, the novel coating composition is colored by incorporating a pigment or dye in the composition. This is preferably accomplished by dispersing the pigment in a mixture or slurry of reactants prior to completing the reaction. Most preferably the pigment is supplied in the form of an aqueous surfactant solution.

As used herein, "pigment" is a general term for various inorganic and organic, natural and synthetic chemical substances and mixtures used to confer color to a substance. A pigment may be white, black, or a color of the spectrum, and as used herein is meant to encompass white, black or a color of the spectrum, although a green color is preferred. A pigment is typically a finely divided powder, usually described as insoluble but wettable. Pigments impart color by either absorbing light or by being luminescent. Similar to pigments are dyes, which are almost always organic and frequently soluble. A dye might be usable in lieu of a pigment if its use would not interfere with the intended purpose of the coating in accordance with the present invention.

In accordance with a preferred embodiment of the present invention, the resultant reaction product has the pigment homogeneously distributed therein to produce a uniform color in the coating composition. Although a homogeneous distribution of the pigment is preferred, pigment may be treated to cluster or clump together so as to take on an non-uniform color pattern, such as polka dots or streaks.

Although not wishing to be bound by any particular theory, it is believed that by having the pigment present during the reaction, the pigment becomes incorporated or entrapped in the reaction product composition, i.e. the magnesium stearate-magnesium oxide, and is not available to discolor equipment, individuals working with the composition or objects in the surrounding environment which may come into contact with the composition. In this regard, the pigment is considered to be entrapped in a matrix of magnesium stearate and magnesium oxide of the resultant composition so as to prevent or substantially minimize the direct exposure of the pigment to foreign objects which could otherwise become colored by the pigment. It has also been discovered that, by including the pigment with the reactants in the reaction mixture, the amount of pigment needed to effect substantially the same color in the composition is advantageously reduced in comparison to dry-mixing the pigment with the composition of magnesium and stearate-magnesium oxide powder. In this regard, it has been discovered that producing a coating composition containing pigment in accordance with the present invention requires up to about 5½ times less pigment than if the pigment were dry-mixed with the composition of magnesium stearate and magnesium oxide.

The present invention is illustrated by the following examples for producing the products and describing the products and their properties.

EXAMPLE 1

This example describes the procedure for reacting stearic acid and magnesium oxide to yield a reaction product including magnesium stearate and 10–15% by weight total magnesium oxide.

The reactor was equipped with a laboratory stirrer, having a variable speed up to 2,000 rpm, and propeller-type, 2 inch diameter blades.

Stearic acid and magnesium oxide were reacted to yield a reaction product of magnesium stearate, water and an excess of magnesium oxide. To this end 50 grams of 60–70 micron, technical grade (95% purity) magnesium oxide, known to exhibit medium reactivity with stearic acid, was introduced into the open-topped reactor.

As used herein, "medium reactivity" describes the property of magnesium oxide attributed in part to this particle size. The smaller the size of the particle, the more surface area there is per volume and weight of the particle. This greater surface area provides for an overall increase in the rate of reaction since the reaction occurs on the surface. The rate of addition during the introduction of magnesium oxide and stearic acid in the first step has been discovered to influence or control the size of the particle formed. The reactivity for this example was desired to be medium to gain certain particular properties of the product, such as those analyzed in Example II below.

1 liter of water and 3.7 grams of technical grade citric acid were then added to the magnesium oxide in the reactor. The resultant mixture was heated to 75° C. and stirred at 1,300 rpm for 30 minutes to evenly distribute the magnesium oxide as a slurry or suspension.

30 grams of commercial grade stearic acid was added to the slurry at the rate of 10 grams/min. and agitated for 30 minutes.

200 grams of stearic acid was then added, also at the same rate, and stirred at 1,500 rpm for 45 minutes at 80°–85° C. to complete the reaction.

Completion of the reaction for purposes of the present invention is determined may be an alkalinity test. More particularly, the test requires that 50 milliliters of filtrate from the slurry should consume a minimum 0.5 milliliters of 10 Normal hydrochloric acid solution.

The amounts of reactants used were calculated stoichiometrically to yield a total magnesium oxide content of approximately 13%.

The resultant slurry was filtered and the recovered product was dried and converted to a powder. The product powder of magnesium stearate-magnesium oxide was white in color, fine, free flowing and odorless.

500 grams of ammonium nitrate prills, having a size of 200–270 SGN (size guide number of a bath, being 100 times the calculated diameter in millimeter of the particle size which divides the mass of all particles in two equal halves), were coated with the magnesium stearate-magnesium oxide reaction product powder, produced above, by tumbling the ammonium nitrate prills with 0.375 grams of the reaction product powder composition of the present invention in a small 10½" diameter by 12 ft. long mechanical steel coating drum for 15 minutes.

The coated ammonium nitrate prills product was characterized as follows:

| | |
|---|---|
| MgO content of coating | 13.5% by weight |
| % coating composition | 0.075% by weight |

EXAMPLE II

A sample product of ammonium nitrate prills coated with the reaction product powder coating composition produced in accordance with the procedure described in Example I was subjected to a "bag test" to compare its caking, hardness and dusting properties relative to those of conventionally coated ammonium nitrate prills.

More particularly, three stacks (identified as Samples A, B and C) with thirty bags in each stack were formed wherein each of the stacks consisted of i) 10 bags, each of which was filled with 25 kilograms of the product of Example I, and II) an additional twenty bags, each of which was filled with 25 kilograins of weighting material. In addition, another three stacks (Samples D, E, F) of thirty bags each were formed wherein each of these stacks consisted of 10 bags containing ammonium nitrate granules coated with conventional magnesium stearate associated with 6.8% MgO(Sample A), ammonium nitrate granules coated with magnesium stearate associated with 20–30% MgO (Sample B), and ammonium nitrate granules coated with clay (Sample C), respectively.

The bags containing coated ammonium nitrate granules were extracted from the stacks A and D after one month and their caking, hardness and dust level properties were examined. Similarly, the bags containing coated ammonium nitrate granules were extracted from the stacks B and E after two months and tested, and finally the remaining bags from stacks C and F were examined after four months.

The products in the examined bags were tested to determine the amount caked, percent hardness of the coated particles, and dust content.

The amount of caking experienced by the product was determined by a visual inspection and the terms used in the table below are deemed to be an accurate characterization of the caking experienced in the samples.

The hardness test involved subjecting the coated particles to ball milling with the results indicating the percent of particles that survived. It is theorized that the hardness test may be affected in part from the result of gained or enhanced lubricating properties of the specially coated particles, resulting in reduced breakage and enhanced ease in handling, such as in pouring.

Determining the dust content involved flowing a known amount of product over downwardly inclined baffles mounted in a box. The dust was suctioned off and weighed.

The results of the testing were as follows:

| Coating MgO content | Amount Caked | Hardness | Dust Level (mg dust/kg product) |
|---|---|---|---|
| 6.8% | Moderate | 92 | 10 |
| 10-15% | Low | 97 | 5 |
| 20-30% | High | 54 | 7 |
| Clay coating | Moderate | 96 | 80 |

The results indicate that if the MgO content in the magnesium stearate coating is less than about 10% or greater than about 15%, the caking and dusting qualities deteriorate.

EXAMPLE III

This example describes a preferred procedure for coloring the coating composition and describes the product.

135 milligrains of Fanal (a trademark of BASF) Green (08330) pigment was mixed with 70 mg of nonionic surfactant (available from the IGEPAL Co. under designation 630) in 25 milliliters of water.

The resultant mixture was added to the reactor with the MgO/catalyst/water charge of reactants used in Example I and subjected to the reaction procedure with stearic acid as described in Example I.

The tinted reaction product powder composition of the present invention was light green in color, fine, freeflowing and odorless. The coloring was uniform throughout the reaction product powder. When handled, the coloring was not transferred onto the hands.

In order to achieve the same color intensity, however, about 742.5 milligrains of Fanal Green pigment was required to be dry mixed with the composition of magnesium stearate magnesium oxide of the present invention.

It has been unexpectedly discovered that by producing a reaction powder product including increased amounts of magnesium oxide, i.e. within the range of 10-15% by total weight, compared to the magnesium oxide content of conventional commercial magnesium stearate, i.e. about 6.8% MgO, the coated substrate is noticeably less dusty and has better anti-caking capability than when coated with conventional magnesium stearate.

As previously stated, by obtaining a good dispersion of the pigment in the slurry of reactants using the surfactant solution and having the pigment present during the reaction, a more uniformly and distinctively colored coating composition is obtained wherein the pigment is entrapped in a matrix of magnesium stearate and magnesium oxide so that the color from the pigment in the coating on the substrate does not significantly discolor equipment or individuals handling the coated substrate, and substantially less pigment is required for this purpose than if the pigment was dry-mixed with the composition of magnesium stearate and magnesium oxide.

In addition to pigments, trace additives can also be added to the reaction mixture to gain the benefit of the known properties of such additives.

Although the above disclosure and examples specify the use of magnesium oxide and stearic acid as reactants and the resultant reaction product composition as magnesium stearate or magnesium stearate-magnesium oxide, other substances for coating chemicals may used in the practice of the present invention so long as their use does not adversely affect the results realized by the practice of the present invention. For example, in place of magnesium, calcium or another Group IIA metal may be used, depending upon the desired end use. Also, oleic acid or an equivalent or otherwise appropriate long-chain carboxylic acid may be substituted for stearic acid depending upon the metal used. Temperatures, amounts and reaction times may also be varied.

Another example of the versatility of the use of the reaction powder product of the present invention is in the field of plastics, particularly extruded plastics technology. The composition of magnesium stearate and magnesium oxide produced in accordance with the present invention has contemplated use in these areas of technology as a lubricant and/or coating which is particularly useful during the manufacture of plastic objects, such as during the extrusion of a plastic articles, eg. plastic pipes. The capability to use a pigmented coating in such processes will result in many advantages which will be appreciated by the artisan. Moreover, the previously discussed technology is useful for coating chemicals other than agricultural fertilizers, and particularly ammonium nitrate which functions as an explosive which, when used in conjunction with fuel oil, is termed "ANFO". Therefore, other suitable substrates contemplated as being useful with the present invention are explosive grade nitrates, as mentioned above, or animal feed materials, such as phosphates, urea, or their derivatives.

Thus the particular substrate for use in accordance with the present invention includes a wide variety of substrates including particles, such as prills and granules, of fertilizer, explosive materials, animal feedstuffs, as well as extruded plastic articles, such as plastic pipes.

It is further understood that although the invention has been specifically described with reference to particular means and embodiments, the foregoing descriptions that of preferred embodiments of the invention. The invention, however, is not limited to the particulars disclosed but extends to all equivalents, and various changes in modifications may be made to the invention without departing from the spirit and scope thereof.

What is claimed is:

1. A process for preparing a composition comprising a carboxylate compound of a metal and oxide of said metal and a pigment entrapped in matrix comprising:
   forming a slurry comprising said oxide, a catalyst, a carboxylic acid and water;
   admixing additional carboxylic acid selected from the group consisting of stearic acid and oleic acid with said slurry;
   adding a pigment to said slurry to form a reaction mixture; and
   digesting said reaction mixture at a sufficient temperature for a sufficient retention time to react substantially all carboxylic acid to form a slurry containing a reaction product composition comprising a carboxylate compound of a metal and an oxide of said metal present in an amount within the range of about 10-15% by weight of said composition, and said pigment whereby transfer of color from said pigment to an object is substantially minimized or prevented.

2. The process of claim further comprising forming an aqueous solution comprising said pigment and adding said pigment in said aqueous solution to said slurry.

3. The process of claim 2, wherein said aqueous solution further comprises a surfactant.

4. The process of claim 3, wherein said surfactant is a non-ionic surfactant.

5. The process of claim 4, wherein said pigment has a green color.

6. The process of claim 1 wherein said catalyst comprises citric acid.

7. The process of claim 1 wherein said carboxylic acid is stearic acid.

8. The process of claim 1 further comprising filtering said slurry composition and converting said reaction product composition filtrate.

9. The process of claim 8, further comprising drying said reaction product composition and converting said reaction product composition powder.

10. The process of claim 1, wherein said reaction mixture is digested at a digestion temperature less than about 85° C.

11. The process of claim 10, wherein said digestion temperature is within the range of about 80° C. -85° C.

12. The process of claim 11,, wherein said slurry of said oxide, said catalyst, said carboxylic acid and water is agitated at a temperature of about 75° C. to disperse said oxide in said slurry.

13. The process of claim 1, wherein said metal is a Group IIA metal.

14. The process of claim 13, wherein said metal is selected from the group consisting of magnesium and calcium.

15. The process of claim 14, wherein said metal is said magnesium.

16. The process of claim 15, wherein said carboxylate compound is magnesium carboxylate.

17. The process of claim 16, wherein said oxide is magnesium oxide.

18. The process of claim 17 wherein said pigment is uniformly distributed throughout said composition.

19. A process of preparing a pigmented color composition comprising:
  forming a slurry comprising a pigment, magnesium oxide, stearic acid and water;
  digesting said slurry under reaction conditions sufficient to produce a reaction product composition comprising magnesium stearate and magnesium oxide present in an amount within the range of about 10–15% by weight of said composition, and pigment entrapped by said magnesium stearate and magnesium oxide so as to substantially prevent color transfer from said pigment to an object with which said composition comes in contact.

* * * * *